(12) United States Patent
Carr et al.

(10) Patent No.: US 7,769,469 B2
(45) Date of Patent: Aug. 3, 2010

(54) INTEGRATED HEATING/SENSING CATHETER APPARATUS FOR MINIMALLY INVASIVE APPLICATIONS

(75) Inventors: Kenneth L. Carr, Woolwich, ME (US);
Robert C. Allison, Rancho Palos Verdes, CA (US)

(73) Assignee: Meridian Medical Systems, LLC, Woolwich, ME (US)

( * ) Notice: Subject to any disclaimer, the term of this patent is extended or adjusted under 35 U.S.C. 154(b) by 1073 days.

(21) Appl. No.: 11/474,883

(22) Filed: Jun. 26, 2006

(65) Prior Publication Data

US 2007/0299488 A1 Dec. 27, 2007

(51) Int. Cl.
*A61B 18/04* (2006.01)
*A61B 18/18* (2006.01)

(52) U.S. Cl. .................. 607/101; 607/100; 607/154; 607/156; 606/33

(58) Field of Classification Search .............. 607/100, 607/156; 600/549
See application file for complete search history.

(56) References Cited

U.S. PATENT DOCUMENTS

| | | | |
|---|---|---|---|
| 4,583,556 A | 4/1986 | Hines et al. | |
| 5,364,336 A | 11/1994 | Carr | |
| 5,531,662 A | 7/1996 | Carr | |
| 5,683,382 A | 11/1997 | Lenihan et al. | |
| 5,688,050 A * | 11/1997 | Sterzer et al. | 374/122 |
| 5,690,614 A | 11/1997 | Carr et al. | |
| 5,974,343 A * | 10/1999 | Brevard et al. | 607/102 |
| 6,424,869 B1 | 7/2002 | Carr et al. | |
| 6,496,738 B2 | 12/2002 | Carr | |
| 6,932,776 B2 | 8/2005 | Carr | |
| 2004/0243004 A1 | 12/2004 | Carr | |
| 2004/0249272 A1 | 12/2004 | Carr | |

* cited by examiner

*Primary Examiner*—Roy D Gibson
*Assistant Examiner*—Kaitlyn E Helling
(74) *Attorney, Agent, or Firm*—Cesari and McKenna, LLP (57) ABSTRACT

Medical catheter apparatus for minimally invasive applications includes a probe for radiating electromagnetic waves of a first frequency capable of heating tissue and detecting thermal emissions from that tissue of a second frequency indicative of tissue temperature. The probe has an inner conductor extending along the probe to a conductive probe tip and a concentric tubular outer conductor having a leading end spaced rearwardly from the probe tip and a closed trailing end shorted to the inner conductor. A dielectric sheath surrounds the outer conductor which sheath has a leading end spaced rearwardly from the leading end of the outer conductor. A diplexer integrated into the probe includes a filter circuit positioned inside the outer conductor and a coupling capacitor connected between a point on the inner conductor and the input of the filter circuit such that the conductors between that point and the shorted trailing end of the outer conductor constitute a quarter wave stub at the second frequency.

43 Claims, 7 Drawing Sheets

INTEGRATED HEATING/SENSING CATHETER APPARATUS FOR MINIMALLY INVASIVE APPLICATIONS

BACKGROUND OF THE INVENTION

This invention relates to a medical catheter apparatus for minimally invasive applications. It relates more particularly to an integrated antenna catheter system which relies on electromagnetic radiation to simultaneously controllably heat, and detect the temperature of, fluid or tissue adjacent to the catheter. By placing the catheter at the region of interest in the body, one can detect, diagnose and treat certain abnormalities associated with tumors, cardiac arrhythmias, benign prosthetic hyperplasia (BPH) and the like. When placed in a patient's vascular system, the catheter can be used to measure temperature or even to raise tissue temperature during heart surgery. Examples of known antenna catheter apparatus of this general type are described in my patents U.S. Pat. Nos. 5,683,382 and 6,932,776.

Obviously in order to perform their functions, such catheters must be small in diameter and quite flexible so that they can be threaded into the body to the target site via various natural passages in the body. They may also be required to facilitate various ancillary processes such as maintenance of the catheter at a selected or constant temperature, display of the target site, irrigation of the target site, etc.

Antenna catheters of the above type are invariably connected via a long cable to an external control unit which includes a transmitter for transmitting electromagnetic energy to the antenna catheter in order to heat fluid or tissue adjacent to the catheter, and a receiver in the form of a radiometer which detects thermal emissions picked up by the antenna catheter and which reflect the temperature of the fluid or tissue being examined. The receiver produces corresponding output signals to control a display which displays that temperature. Those same signals may also be used to control the transmitter to maintain a selected heating profile.

For such apparatus which detect thermal emissions in the microwave range which is of primary interest here, the receiver is usually a Dicke-type radiometer. Such a radiometer is a comparison radiometer system which utilizes a switch to alternately connect the antenna (the unknown temperature to be detected) and the reference temperature, which may be a stable noise source or a temperature sensor with in the catheter.

Every component of such a radiometer generates noise power that contributes to the overall noise of the system. Therefore, the total apparatus output contains not only noise received by the antenna, but also noise generated within the apparatus itself. Such variations within the apparatus can produce spurious output signal fluctuations that are sometimes greater than the signal level to be measured. To overcome these gain variations, Dicke developed the common load comparison radiometer. This configuration greatly reduces the effects of short-term gain fluctuations in the radiometer. More particularly, the switch provides a mechanism to allow both the reference and the unknown signals to pass through the apparatus essentially at the same time relative to the expected gain drift in the radiometer's amplifiers such that any drifting gain will be applied equally to both the antenna and reference signals.

Since the radiometer input is switched at a constant rate by the Dicke switch between the antenna and the constant-temperature reference load, the switched or modulated RF signal should, therefore, be inserted at a point prior to RF amplification in the radiometer and as close to the antenna as possible. Any component or transmission line located between the unknown temperature being detected and the Dicke switch can introduce an error. One such error source is the long coaxial cable which connects the antenna to the radiometer.

More particularly, the temperature of that cable contributes to the temperature measurement. The cable temperature is usually not known and varies along the length of the cable. That portion of the cable within the body will be at body temperature, whereas the segment of the cable outside the body will be at room temperature. All of these parameters may vary with the flexing and depth of insertion into the body of the probe. Also when the apparatus includes a transmitter, power is absorbed by the cable, causing the cable to be heated. If the loss in the cable is, say, 3 dB (which could easily be the case), one half of the antenna noise power comes from the desired tissue or fluid volume being examined and the rest results from in the cable.

Thus while errors common to both measurements, i.e. the unknown temperature versus the reference temperature, are cancelled in a Dicke-type radiometer, any changes or errors between the unknown and the Dicke switch affect only the unknown temperature measurement and are not common to both measurement paths.

Thus to achieve accurate measurement, it is highly desirable to minimize the losses between the antenna and the radiometer in order to improve the performance and reliability of the overall apparatus, without increasing the size, weight and cost thereof.

SUMMARY OF THE INVENTION

Accordingly the present invention aims to provide a minimally invasive antenna catheter apparatus for simultaneously controllably heating and sensing the temperature of fluid or tissue in a human or animal body.

Another object of the invention is to provide such apparatus which includes an antenna catheter which may be inserted into a patient and an external control unit and whose designs eliminate the need for a long, lossy coaxial cable between the catheter and the external unit.

A further object of the invention is to provide a minimally invasive temperature sensing apparatus comprising an antenna catheter and a receiver in the form of a radiometer wherein the radiometer is integrated right into the catheter.

Still another object of the invention is to provide an integrated antenna catheter including a built-in diplexer and microwave receiver which, when connected to an external control unit containing a transmitter, can simultaneously heat and detect the temperature of fluid or tissue adjacent to the catheter.

Other objects will, in part, be obvious and will, in part, appear hereinafter.

The invention accordingly comprises the features of construction, combination of elements and arrangement of parts which will be exemplified in the following detailed description and the scope of the invention will be indicated in the claims.

Briefly, the present apparatus comprises an antenna catheter for insertion into a human or animal patient. The catheter, sometimes also referred to as a probe, may be connected to an external control unit which may include a transmitter and a display. As usual, the apparatus also includes a receiver, preferably a Dicke-type radiometer. However, instead of incorporating the receiver into the external control unit as is done conventionally, all components of that receiver are integrated right into the catheter and preferably, but not necessarily, the transmitter transmits RF signals, i.e. below 300 MHz. Not only does this minimize the electrical distance between the antenna and the receiver, it also eliminates the need for long a coaxial cable which suffers signal losses and gives rise to measurement errors as described above. Therefore, the present apparatus has a higher signal-to-noise ratio and sensitivity than prior comparable apparatus of this type, yet is simpler and less expensive to make and maintain.

When the apparatus is intended to heat tissue as well as to sense the temperature thereof, a diplexer is also integrated right into the catheter as will be described in detail later so that the same catheter can simultaneously radiate energy received from an external transmitter at one frequency to heat tissue and detect thermal emissions from that tissue at a different frequency and which are indicative of tissue temperature.

BRIEF DESCRIPTION OF THE DRAWINGS

For a fuller understanding of the nature and objects of the invention, reference should be made to the following detailed description taken in connection with the accompanying drawings, in which.

DESCRIPTION OF A PREFERRED EMBODIMENT

Figure 1:
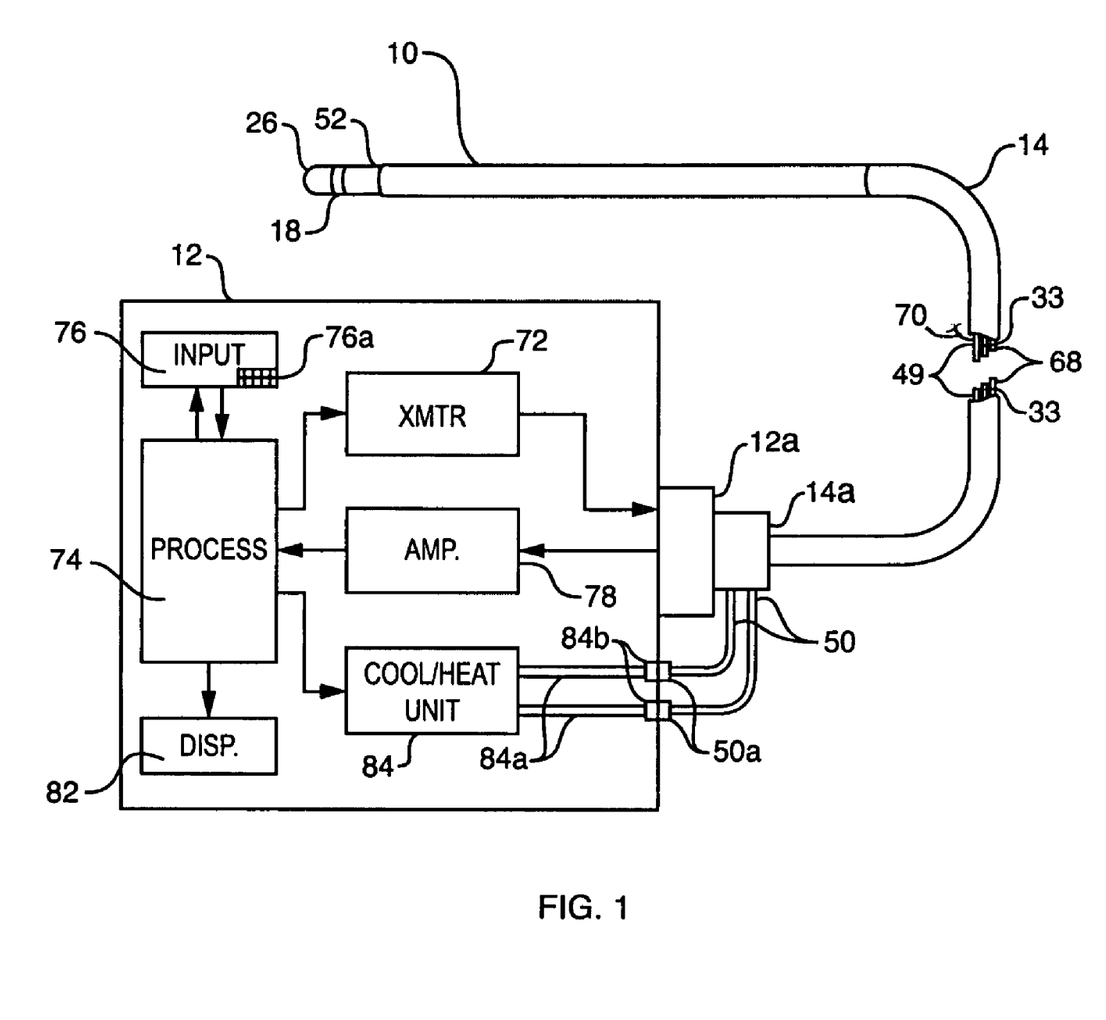
FIG. 1 is a diagrammatic view of integrated catheter apparatus for minimally invasive applications incorporating an antenna catheter for controlled heating and temperature sensing.

Referring to FIG. 1 of the drawings, the apparatus comprises a minimally invasive flexible antenna catheter or probe 10 adapted to be threaded into a patient via a natural or incised passage in the patient's body, and an external control unit 12. The catheter is connected to unit 12 by a flexible cable 14 having an end connector 14a that connects to a mating connector 12a on unit 12. Typically, catheter 10 may be only 0.5 to 1.0 inch long and 0.08 to 0.10 inch in diameter.

Figure 2:
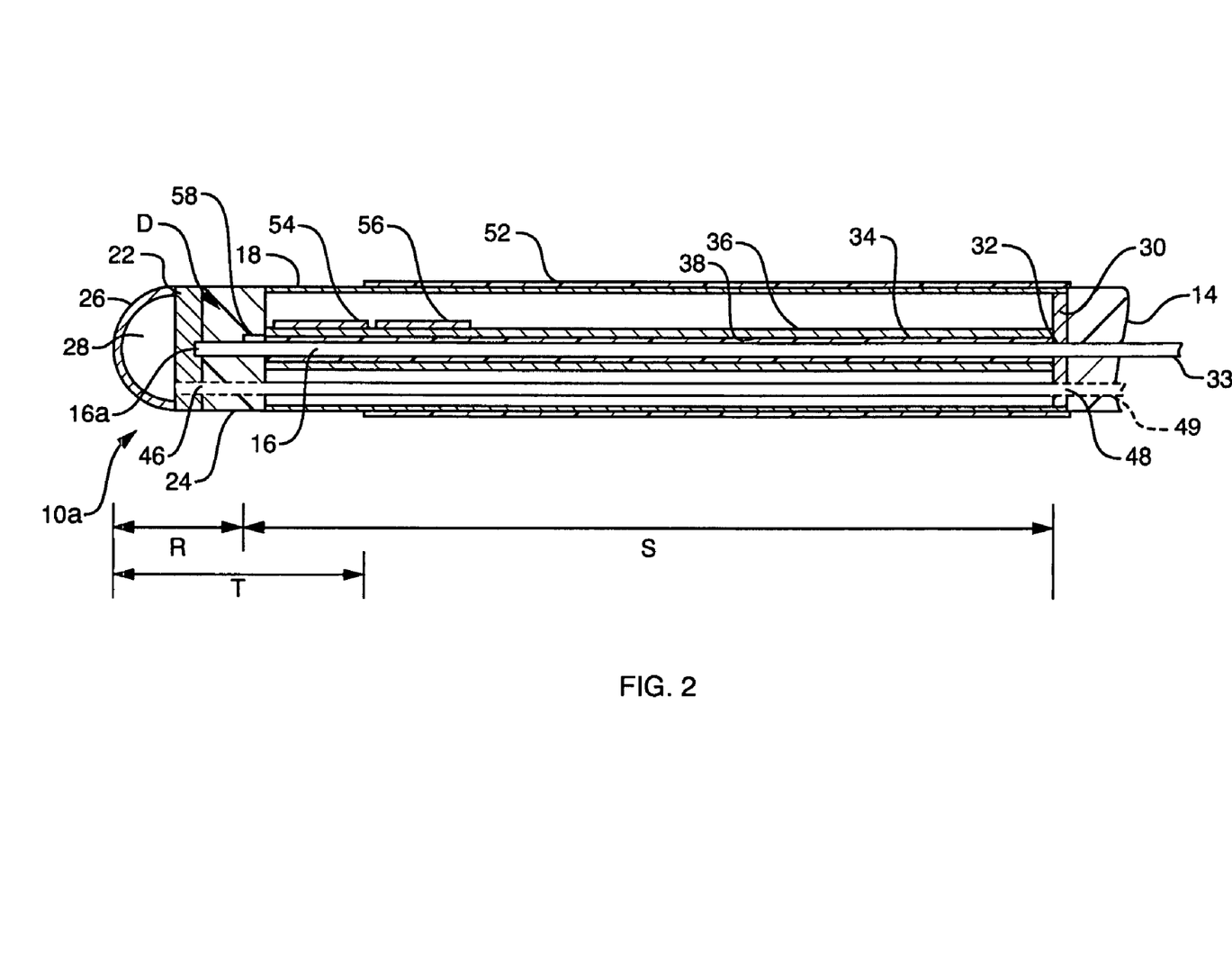
FIG. 2 is a fragmentary longitudinal sectional view on a larger scale showing the antenna catheter in FIG. 1 in greater detail.
Figure 3:
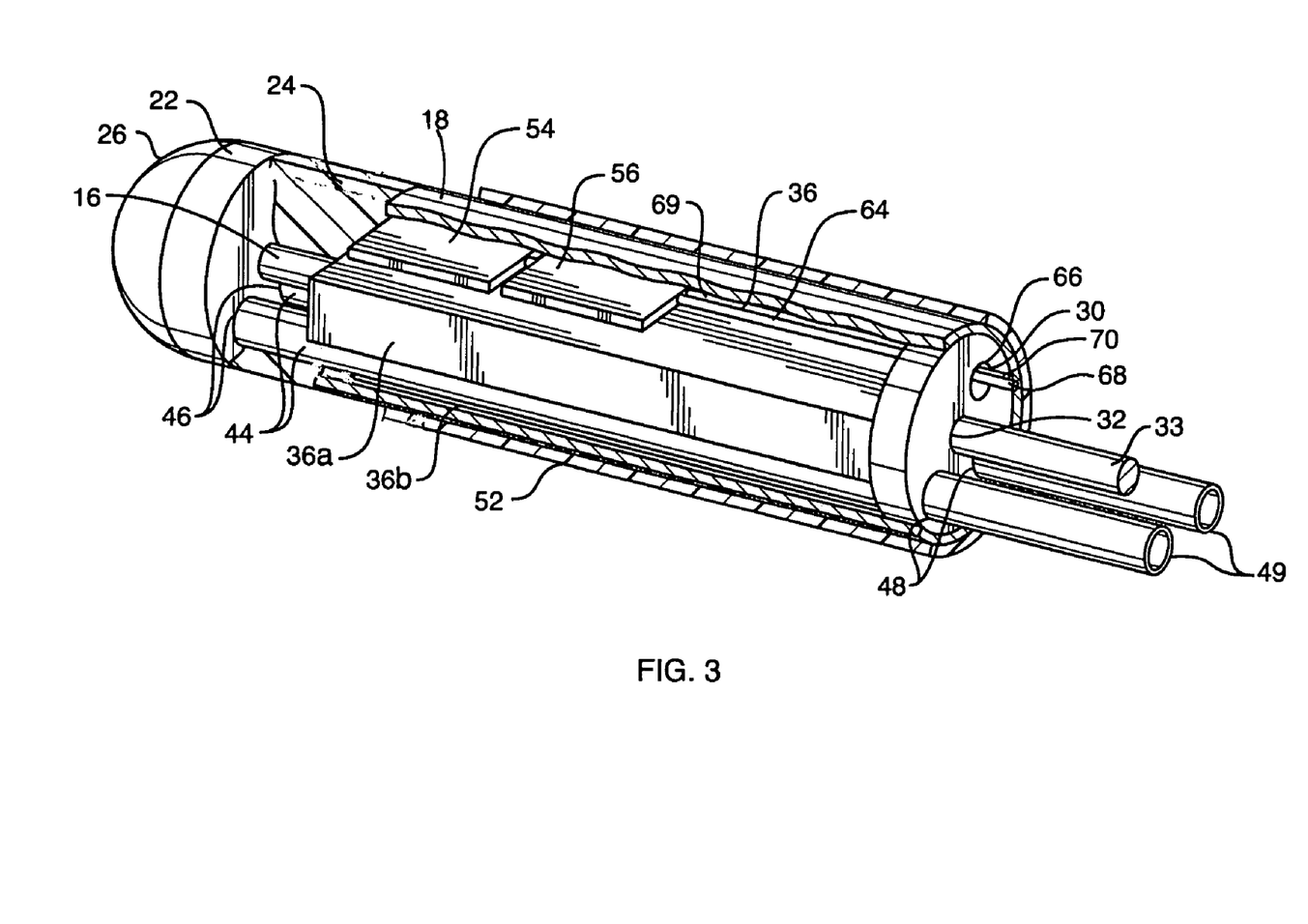
FIG. 3 is a fragmentary perspective view with parts broken away on a still larger scale of the FIG. 2 catheter.

Referring now to FIGS. 2 and 3, catheter 10 includes an inner conductor 16 and a coaxial tubular outer conductor 18. Conductor 16 is longer than conductor 18 and its front or leading end 16a is connected by solder, welding, etc. to the center of a conductive discoid toe plate 22 spaced in front of the outer conductor 18 which space is filled by a discoid dielectric spacer member 24. A hemispherical conductive shell 26 is mounted to the front face of toe plate 22. Together they form the conductive leading end or tip 10a of catheter 10. Shell 26 also defines a fluid-tight space 28 between the shell wall and the toe plate.

The rear or trailing end of outer conductor 18 is closed by a discoid heel cap 30 soldered or welded to conductor 18 and to the rear end 16b of inner conductor 16 which end extends into a small opening 32 at the center of heel cap 30. The rear end of center conductor 16 is also connected to the leading end of an inner conductor 33 of cable 14. Those two conductors meet in opening 32 with the cable end being anchored to heel cap 30.

Figure 4:
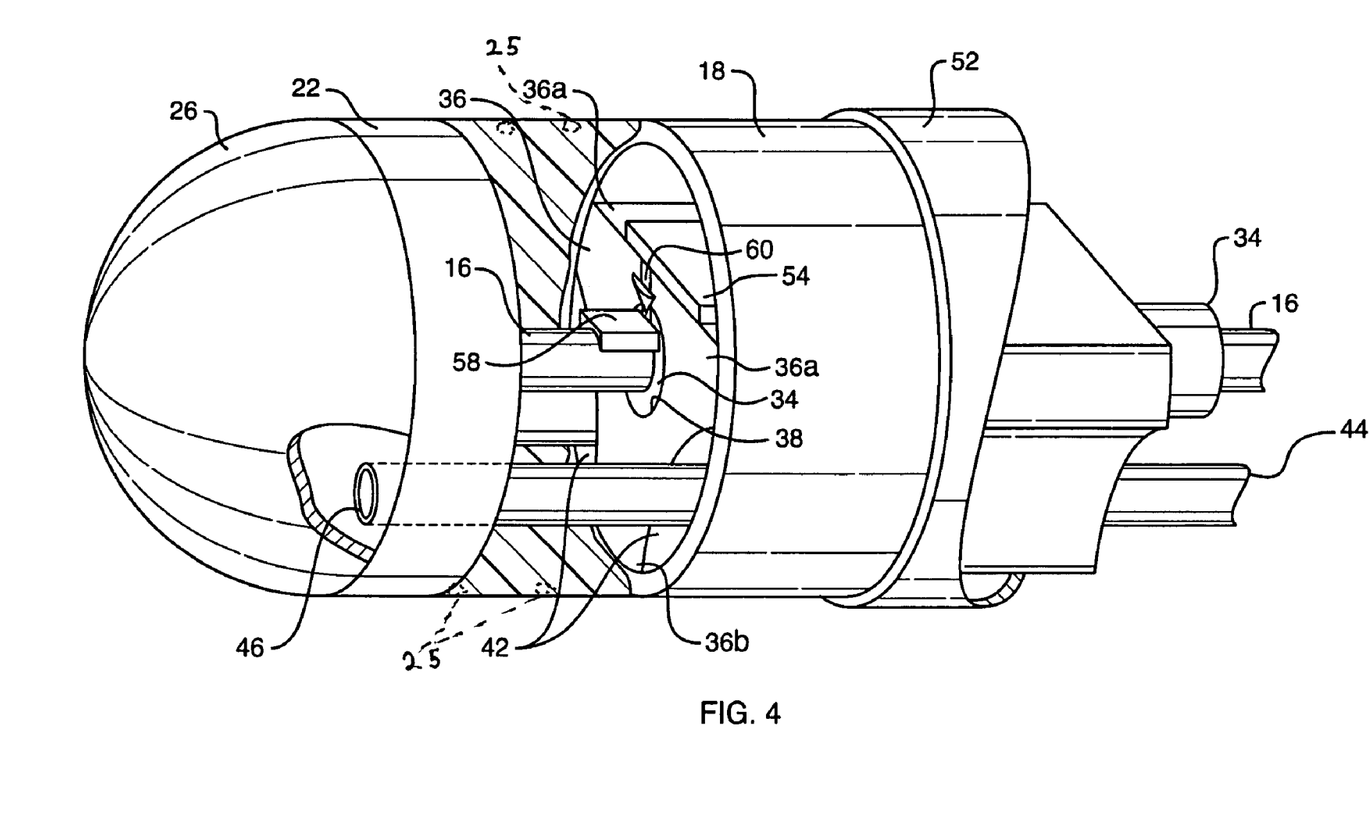
FIG. 4 is a similar view on an even larger scale showing a portion of the FIG. 2 catheter in greater detail.

As best seen in FIGS. 2 and 4, the segment of inner conductor 16 within the outer conductor 18 carries a dielectric sleeve 34 and is supported within conductor 18 by a conductive insert 36 which fits snugly in, and extends the length of, conductor 18. The conductor 16 and its sleeve 34 extend along an axial passage 38 in the insert. Insert 36 is in contact with both outer conductor 18 and heel cap 30.

As best seen in FIGS. 3 and 4, insert 36 is generally T-shaped in cross-section having a pair of arms 36a, 36a and a leg 36b which define, along with outer conductor 18, a pair of longitudinal passages 42, 42 which extend the length of the insert 36. These passages are able to accommodate a pair of tubes 44 whose forward ends are secured in a pair of holes 46, 46 in toe plate 22. The tubes extend along passages 42, 42 into through-holes 48, 48 in heel cap 30 where they communicate with passages 49, 49 in cable 14.

The tubes 44 provide a fluid path to and from the space 28 at the catheter tip 10a so that a fluid may be circulated through the catheter in order to cool the catheter tip or maintain it at a selected temperature. Actually, the insert 36 through which those tubes pass constitutes a heat sink. Therefore, the tubes may open into insert passages 42, 42 so that the entire catheter and its contents can be maintained at the temperature of that fluid. As shown in FIG. 1, the passages 49, 49 in cable 14 extend to connector 14a where they communicate with hoses 50 terminated by connectors 50a releasably coupled to control unit 12.

Of course, the insert passages 42, 42 and tubes 44, 44 could also be used for other purposes. For example a small hole 26 may be provided in shell 26 so that an irrigation fluid delivered by one or both tubes may be ejected from the catheter tip 10a. Also, the passages and/or tubes may accommodate small wires leading to a temperature sensor, ultrasonic transducer or other electrical device in the space 28 at the catheter tip, depending upon the particular application.

As best seen in FIGS. 2 and 3, a sheath 52 of a dielectric material e.g. PTFE, surrounds the outer conductor 18 of catheter 10. However, that sheath does not extend all the way to the front or leading end of the conductor, but rather terminates at a selected distance therefrom for reasons that will become apparent. The rear or trailing end of sheath 52 blends into cable 14 so that there is essentially no stepped boundary between the two, thereby enabling the catheter be threaded easily into a patient.

Referring now to FIGS. 2 to 4, a filter circuit 54 and a microwave radiometer circuit 56, preferably in the form monolithic microwave integrated circuit chips (MMICS), are mounted to the top of insert 36 which thus functions as a carrier and heat-sink for those chips. Also, mounted directly to the inner conductor 16 just ahead of insert 36 is a coupling capacitor 58 which is recessed into the spacer member 24. One terminal of capacitor 58 is connected electrically to conductor 16 and the other is connected by way of a lead strip 60 to filter circuit 54 which is, in turn, connected to radiometer circuit 56. The output signal from radiometer circuit 56 as well as certain bias and control voltages are carried on conductor group 64 which extends along the top of insert 36 and exits the catheter through a hole 66 in heel cap 30. There, those conductors join corresponding conductors 68 (FIGS. 1 and 3) which extends along cable 14 to control unit 12. Also, a ground return conductor 69 from circuit 56 connects to a corresponding conductor 70 in cable 14.

Preferably radiometer circuit 56 operates at a frequency in the microwave range, e.g 1 GHz to 26 GHz, most preferably at a center frequency of 4 GHz. A conventional Dicke-type radiometer circuit is disclosed in my patent U.S. Pat. No. 4,557,272. Similar radiometer designs on a chip are available from Meridian Medical Systems, Inc., the assignee of this application.

Referring to FIG. 1, the control unit 12 includes a transmitter or generator 72 which delivers power to catheter 10 by way of cable 14. The output signal from transmitter 72 has a frequency that is different from and preferably much lower than the radiometer frequency. The illustrated transmitter has an output in the RF frequency range, i.e. below 300 MHz, most preferably 500 KHz, so that cable 14 does not have to be a coaxial cable thereby enabling it to be more flexible and less lossy than a coaxial cable. If that is not a problem for a given application, generator 72 could transmit at a higher frequency in the microwave range. Transmitter 72 is controlled by a processor 74 which receives instructions via control buttons 76a on an operator control panel 76 in unit 12.

The control unit 12 also includes an amplifier 78 which receives the temperature-indicating output signal from radiometer circuit 56 via conductors 68 in cable 14. Amplifier 78 conditions that signal and routes it to processor 74 which produces a corresponding control signal for controlling the output of transmitter 72. Processor 74 may also apply that signal to a display 82 which can display in real time the temperature of the fluid or tissue being probed by catheter 10.

Of course, display 82 can also display other parameters related to the proper operation of the apparatus such as transmitter output power, reflected power, catheter temperature, room temperature, elapsed time, etc.

Preferably also, control unit 12 includes a heating/cooling unit 84 controlled by processor 74 and connected via hoses 84a, 84a to fittings 84b, 84b to which connectors 50a, 50a are coupled. This enables unit 84 to circulate a fluid through catheter 10 to maintain the catheter at a selected temperature above or below room temperature or to follow a selected temperature regime, depending upon the particular application.

Referring now to FIG. 2, basically the inner conductor 16 in catheter 10 constitutes an RF transmission line terminated by the conductive rounded tip 10a. The transmission line is operated at the output signal frequency of transmitter 72, e.g. 500 KHz. When transmitter 72 is operative, the transmission line will radiate energy for heating only from the uninsulated segment of the catheter between the catheter tip 10a and the leading end of the dielectric sheath 52. Thus, that segment constitutes an RF heating or transmitting antenna T whose length is determined by the forward extent of sheath 52 on outer conductor 18. In other words, increasing the length of sheath 52 will reduce the exposed length of conductor 18, i.e. the surface that could contact tissue, and, in turn, reduce the antenna T length. Since the outer conductor 18 is at the same RF potential as conductor 16, it can provide an RF path between the antenna T and transmitter 72.

Referring to FIGS. 2 and 4, the conductive catheter tip 10a also comprises a temperature sensing microwave receiving antenna R which can pick up thermal emissions from tissue adjacent to the catheter 10. The segment of conductor 16 from the tip 10a to its junction with capacitor 58 comprises the microwave receiving path and this path continues along a lead strip 60 to filter circuit 54 and thence to radiometer circuit 56. It should be noted that while conductor 33 is basically an extension of conductor 16, it conducts only the RF signal via outer conductor 18, while conductor 16 conducts both the RF and microwave signals.

In some applications, it may be desirable to bridge the dielectric spacer member 24 with a small helical wire (2-4 turns) wound about member 24 in grooves therein as shown in phantom at 25 in FIG. 4 to connect tip 10a to conductor 18. This improves the RF heating pattern of antenna T without materially degrading the microwave antenna pattern of receiving antenna R.

To enable catheter 10 to simultaneously heat (transmit) and detect temperature (radiometrically sense), a passive diplexer D is integrated into catheter 10 in order to block the transmitter signals from the microwave receiving path and isolate the microwave signals from the transmitter. The diplexer D is formed by the a quarter-wave ($\lambda_R/4$) shorted stub 1 constituted by the segment of catheter 10 extending from capacitor 58 (or more specifically its connection to conductor 16 to the heel cap 30. This quarter wave stub S should be tuned to the frequency of the radiometer circuit 56, e.g. 4 GHz.

The tuned length of the stub S, i.e. the catheter segment between capacitor 58 and heel cap 30, is determined by the dielectric constant of the material in sleeve 34 as well as the radiometer frequency. For example, at a radiometer frequency of 4 GHz, when sleeve 34 is of PTFE (K=2.1), the stub length should be 0.5 inch. On the other hand, when a K=9 material is used, the stub length would be reduced to 0.25 inch. For an intermediate length, e.g. 0.38 inch, a K=3.8 material would be used.

Figure 5:
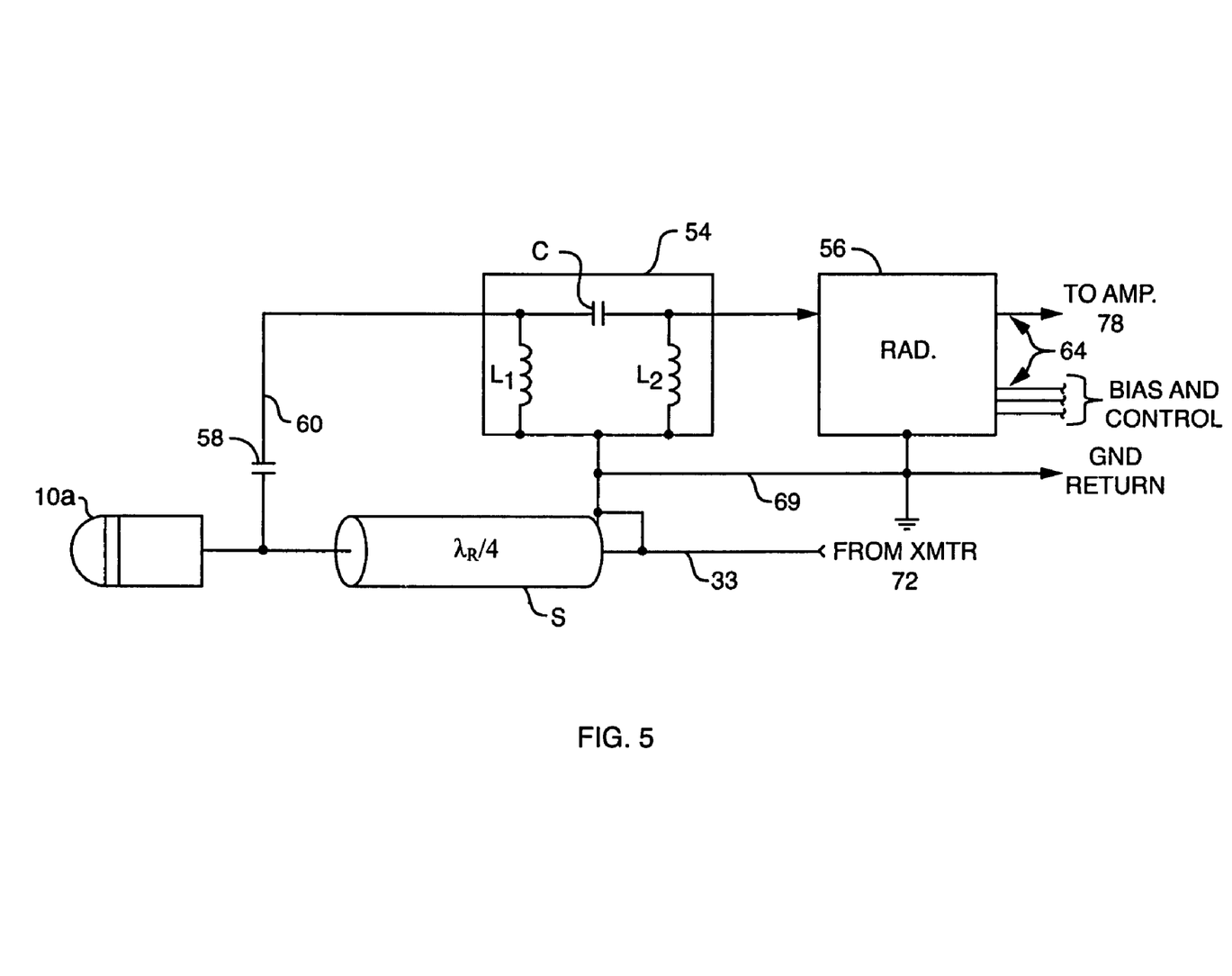
FIG. 5 is a schematic diagram showing certain electrical components incorporated into the FIG. 2 catheter.

FIG. 5 is a schematic diagram showing the components of the diplexer D including the quarter wave stub S, the coupling capacitor 58, the lead strip 60 as well as the components of the band pass filter circuit 54. As seen there, the present catheter 10 design introduces the stub S, tuned to the radiometer frequency, into the transmit path from transmitter 72 to tip 10a. The stub S and inductance $L_1$ in circuit 54 form a low pass filter that isolates the higher frequency (4 GHz) signal from the RF path to transmitter 72. On the other hand, the capacitor C and inductance $L_2$ together constitute a high pass filter that blocks the lower frequency (500 KHz) transmitter signal from the signal-receiving path to radiometer circuit 56. In some applications it may be desirable for the circuit 54 chip to include elements of the radiometer circuit 56. Placing parts of the radiometer on separate chips prevents feedback caused by having too much amplifier gain on a single chip.

In FIGS. 2 and 4 we show capacitor 58 mounted directly to the center conductor 16. However, it could be incorporated into filter circuit 54 in which case the lead strip 60 in FIG. 4 would extend from conductor 16 directly to circuit 54.

Figure 6:
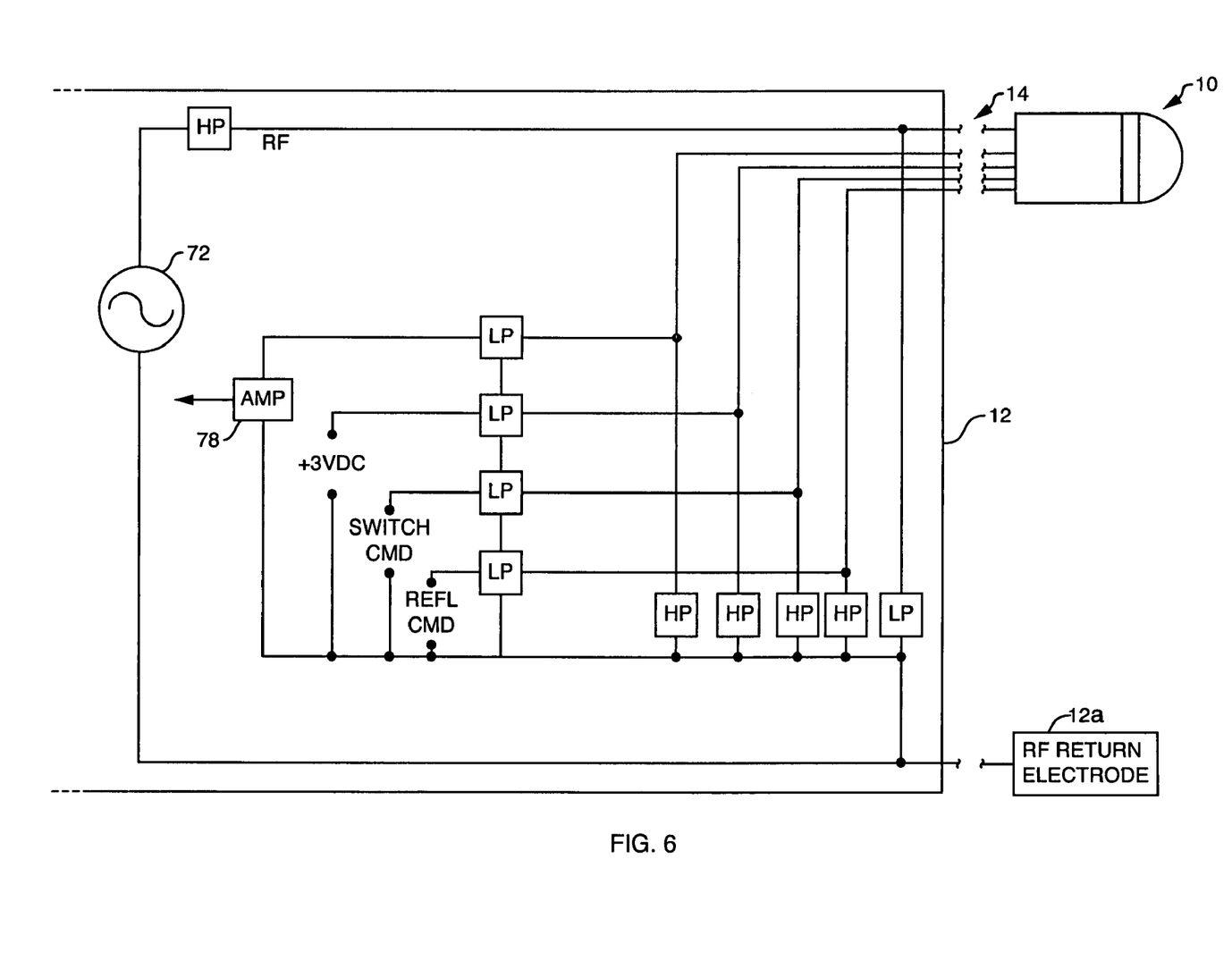
FIG. 6 is a similar diagram showing certain components of the apparatus' control unit.

Refer now to FIG. 6 which shows the control unit 10 in somewhat greater detail. It includes various high pass (HP) and low pass (LP) filters which together form a backend diplexer to isolate the various signals being sent to and from catheter 10 all of which signals are transmitted along dedicated conductors in cable 14. Since the illustrated backend diplexer is only one of the many that could be incorporated into unit 10 and does not comprise the invention here, it will not be described in detail. Suffice it to say that the RF ground conductor 70 from catheter 10 leads to a grounding electrode 12a connected to unit 12. When the apparatus is in use, that electrode is placed in contact with the patient's skin to provide a RF ground return path between the catheter and the patient.

Figure 7:
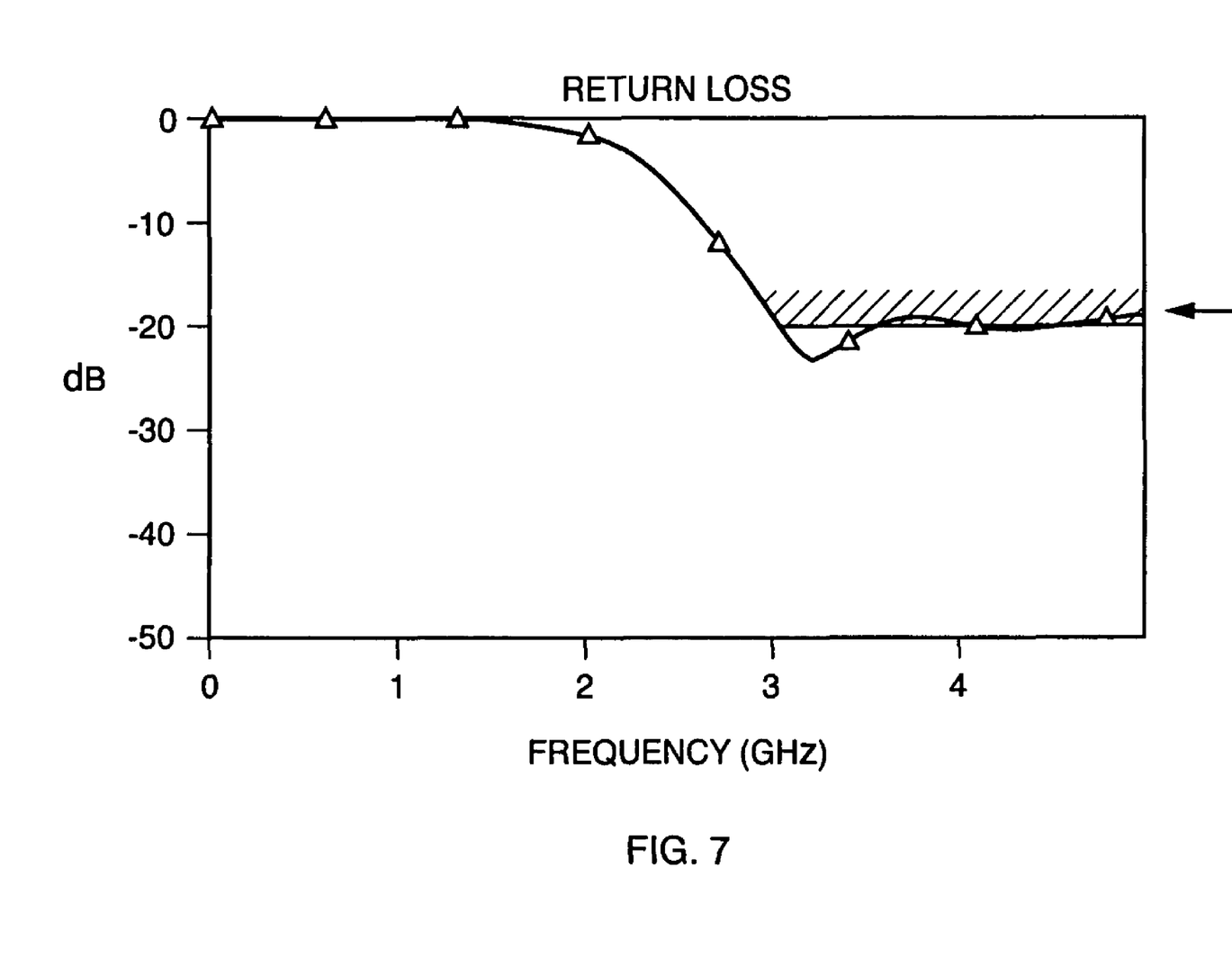
FIG. 7 is a graphical diagram showing the return loss of the FIG. 2 antenna catheter.

FIG. 7 is a graph showing the performance of the diplexer D. As seen there, it provides a good impedance match, i.e. greater than 20 dB, at a receive frequency of 4 GHz, while blocking or rejecting frequencies below 1 GHz including the 500 KHz transmitter frequency.

The above described construction enables essentially the same antenna components to transmit and receive signals simultaneously that can both heat tissue or fluid and detect the temperature of that tissue or fluid in real time, thus enabling the performance of various medical procedures discussed at the outset. The fact that the diplexer and radiometer are incorporated right into the catheter or probe 10 without materially increasing the size and/or stiffness of the catheter enables the apparatus to provide very precise and noise-free temperature measurements in a minimum amount of time.

It will also be seen from the foregoing that my catheter apparatus provides a particularly efficient and effective means for detecting the temperature of tissue or fluid in a human or animal body in order to monitor and/or heat such tissue in a controlled manner. Even though the catheter incorporates transmitting and receiving antennas, an entire microwave radiometer and a diplexer to electrically isolate the transmitter from the receiver, the catheter is still quite small and flexible so that it can be used in many minimally invasive medical applications.

It will thus be seen that the objects set forth above, among those made apparent from the preceding description, are efficiently attained. Also, certain changes may be made in the above construction without departing from the scope of the invention. For example, in some applications, the transmitter 76 could transmit in the microwave region. In that event, however, cable 14 would be a coaxial cable which would make it less flexible and more lossy. Also, of course, if the catheter is to be used only for detection, the diplexer including stub S and circuit 54 could be omitted.

Therefore, it is intended that all matter contained in the above description or shown in the accompanying drawings shall be interpreted as illustrative and not in a limiting sense.

It is also to be understood that the following claims are intended to cover all of the generic and specific features of the invention described herein.

The invention claimed is:

1. Medical catheter apparatus for radiating electromagnetic waves of a first frequency capable of heating tissue and detecting electromagnetic waves of a second frequency emitted by said tissue indicative of tissue temperature, said apparatus comprising a catheter including
a center conductor having a leading end comprising an antenna and a trailing end for connection to a signal transmission path;
a quarter-wave stub between the leading and trailing ends of the center conductor and tuned to said second frequency, and
a filter circuit inside the catheter and comprising a signal receiving path, said filter circuit having an input electrically coupled to a selected location on the center conductor between the antenna and the stub, and an output, said stub and filter circuit together constituting a diplexer for blocking first frequency signals from the signal receiving path and second frequency signals from said signal transmitting path.

2. Medical catheter apparatus for radiating electromagnetic waves of a first frequency capable of heating tissue and detecting electromagnetic waves of a second frequency emitted by said tissue indicative of tissue temperature, said apparatus comprising a catheter including
a center conductor having a leading end comprising an antenna and a trailing end for connection to a signal transmission path;
a quarter-wave stub between the leading and trailing ends of the center conductor and tuned to said second frequency, said stub including
a segment of the center conductor extending rearwardly from said location and a tubular outer conductor concentric to said segment and having a leading end located adjacent to said location and a trailing end;
a conductive member at the trailing end of the outer conductor that short circuits the inner and outer conductors, and
a dielectric sleeve interposed between said segment and the outer conductor along substantially the entire lengths thereof, the length and dielectric constant of said sleeve being selected so as to tune the quarter wave stub to said second frequency, and
a filter circuit inside the catheter and comprising a signal receiving path, said filter circuit having an input electrically coupled to a selected location on the center conductor between the antenna and the stub, and an output, said stub and filter circuit together constituting a diplexer for blocking first frequency signals from the signal receiving path and second frequency signals from said signal transmitting path.

3. The apparatus defined in claim 2 and further including a dielectric sheath surrounding the outer conductor, said sheath having a leading end spaced rearwardly from the leading end of the outer conductor and extending to the trailing end of the outer conductor.

4. The apparatus defined in claim 2 and further including an electrically conductive insert snugly received in said catheter between said sleeve and the outer conductor, said insert extending from the leading end to the trailing end of the outer conductor.

5. The apparatus defined in claim 4 wherein the insert is also thermally conductive.

6. The apparatus defined in claim 5 wherein the filter circuit comprises at least one integrated circuit chip mounted to the insert so that the insert constitutes a heat sink for said chip.

7. The apparatus defined in claim 6 and further including a radiometer circuit in the form of at least one monolithic microwave integrated circuit (MMIC) chip mounted to said insert, said MMIC chip also comprising said signal receiving path.

8. The apparatus defined in claim 7 and further including a cable having a leading end anchored to said stub, said cable including a first connector connected to the trailing end of said center conductor in said signal transmitting path and a second connector connected to the output of the radiometer circuit in said signal receiving path, said cable also having a trailing end terminated by a connector.

9. The apparatus defined in claim 2
wherein the leading end of the center conductor is rounded and has a maximum diameter that is substantially the same of that of the outer conductor, and
further including a discoid dielectric spacer member encircling the center conductor and extending substantially from the leading end of the center conductor to the leading end of the outer conductor.

10. The apparatus defined in claim 9 and further including a small bridging wire extending along the spacer member and electrically connecting the leading ends of the center and outer conductors.

11. The apparatus defined in claim 2 wherein the leading end of the center conductor has a hollow interior, and
further including at least one fluid path leading from the hollow interior of the center conductor along the catheter to the heel cap.

12. The apparatus defined in claim 1 wherein said stub is tuned to a second frequency in the range of 1 to 26 GHz.

13. Medical catheter apparatus comprising a probe for radiating electromagnetic waves of a first frequency capable of heating tissue and detecting thermal emissions from said tissue of a second frequency indicative of tissue temperature, said probe including an inner conductor extending along said probe to a conductive probe tip;

a tubular outer conductor spaced radially out from the inner conductor and having a leading end spaced rearwardly from the probe tip and a trailing end shorted to the inner conductor;

a dielectric sheath surrounding the outer conductor, said sheath having a leading end spaced rearwardly from the leading end of the outer conductor, and a diplexer, said diplexer including a filter circuit positioned inside the outer conductor, said filter circuit having an input coupled to a selected location on the inner conductor, said conductors between said point and the trailing end of the outer conductor constituting a quarter wave stub at said second frequency.

14. Medical catheter apparatus comprising a probe for radiating electromagnetic waves of a first frequency capable of heating tissue and detecting thermal emissions from said tissue of a second frequency indicative of tissue temperature, said probe including an inner conductor extending along said probe to a conductive probe tip;

a tubular outer conductor spaced radially out from the inner conductor and having a leading end spaced rearwardly from the probe tip and a trailing end shorted to the inner conductor;

an electrically conductive insert within the outer conductor and extending between the leading and trailing ends thereof, said insert having an axial passage for receiving the inner conductor;

an electrical insulator between the inner conductor and the insert;

a dielectric sheath surrounding the outer conductor, said sheath having a leading end spaced rearwardly from the leading end of the outer conductor, and a diplexer, said diplexer including a filter circuit positioned inside the outer conductor, said filter circuit having an input coupled to a selected location on the inner conductor, said conductors between said point and the trailing end of the outer conductor constituting a quarter wave stub at said second frequency.

15. The apparatus defined in claim 14 wherein the filter circuit is comprised of an integrated circuit chip mounted to the insert.

16. The apparatus defined claim 15 and further including a microwave radiometer circuit comprised of a microwave integrated circuit chip mounted to the insert, said microwave integrated circuit chip including the filter circuit and having an output for delivering a temperature-indicating signal to an external control unit.

17. The apparatus defined in claim 16 and further including an external control unit including a transmitter for transmitting signals at said first frequency and a processor for controlling the transmitter in response to said temperature-indicating signals from the radiometer circuit, and a cable connected between the probe and the control unit, said cable including a first conductor connecting the transmitter to said inner conductor and a second conductor connecting the radiometer output to the processor.

18. The apparatus defined in claim 17 wherein the control unit also includes a display controlled by the processor in response to the temperature-indicating signals from the radiometer circuit.

19. The apparatus defined in claim 17 wherein the cable is a non-coaxial cable and the transmitter transmits at a first frequency in the RF range.

20. The apparatus defined in claim 17 wherein the transmitter transmits at a first frequency less than 300 MHz and the radiometer circuit operates at a second frequency of 1 to 26 GHz.

21. The apparatus defined in claim 17 wherein the cable is a coaxial cable and the transmitter transmits at a first frequency in the microwave range.

22. The apparatus defined in claim 14
wherein the probe tip is hollow, and
further including at least one passage leading from the interior of the probe tip along the insert past the trailing end of the outer conductor.

23. The apparatus defined in claim 22 wherein the insert is thermally conductive so that it can function as a heat sink when a heating/cooling fluid is flowed to the interior of said tip through said at least one passage.

24. The apparatus defined in claim 13
wherein the probe tip is rounded and has a maximum diameter that is substantially the same as that of said outer conductor, and
further including a dielectric spacer member filling the space between the catheter tip and the leading end of the outer conductor.

25. Medical catheter apparatus comprising a probe for radiating electromagnetic waves of a first frequency capable of heating tissue and detecting thermal emissions from said tissue of a second frequency indicative of tissue temperature, said probe including an inner conductor extending along said probe to a conductive probe tip;

a tubular outer conductor spaced radially out from the inner conductor and having a leading end spaced rearwardly from the probe tip and a trailing end shorted to the inner conductor, said probe tip being rounded and having a maximum diameter that is substantially the same as that of the outer conductor;

a dielectric spacer member filling the space between the catheter tip and the leading end of the outer conductor;

a dielectric sheath surrounding the outer conductor, said sheath having a leading end spaced rearwardly from the leading end of the outer conductor;

a diplexer, said diplexer including a filter circuit positioned inside the outer conductor, said filter circuit having an input coupled to a selected location on the inner conductor, said conductors between said point and the trailing end of the outer conductor constituting a quarter wave stub at said second frequency, and a small wire extending along the spacer member and electrically connecting the probe tip to the leading end of the outer conductor.

26. A medical catheter apparatus comprising
an inner conductor having a front end and a rear end;
a tubular outer conductor spaced radially out from the inner conductor and having a trailing end and a leading end spaced rearwardly from said front end of the inner conductor to form an antenna;

a conductive insert received in said outer conductor and extending between the leading and trailing ends thereof, said insert being in electrical contact with the outer conductor and having an axial passage receiving the inner conductor and a flat surface spaced from the outer conductor;

an insulator electrically insulating the insert from the inner conductor therein;

a receiving circuit chip mounted to said surface, said receiving circuit chip having an input and an output, and a circuit path coupling the inner conductor to said input.

27. The apparatus defined in claim 26 wherein said circuit path includes a filter circuit mounted to said surface and connected between said inner conductor and said chip.

28. The apparatus defined in claim 26 wherein the front end of the inner conductor has substantially the same diameter as the leading end of the outer conductor.

29. The apparatus defined in claim 28 and further including a dielectric spacer extending between the front end of the inner conductor and the leading end of the outer conductor.

30. The apparatus defined in claim 29 and further including a wire bridging the spacer and connecting the respective front and leading ends of the inner and outer conductors.

31. The apparatus defined in claim 29
wherein the front end of the inner conductor has a hollow interior and
further including at least one passage extending from the interior of the inner conductor through said spacer and along said insert at least to the trailing end of the outer conductor.

32. The apparatus defined in claim 26 wherein the insert has a generally T-shaped cross section.

33. The apparatus defined in claim 26 wherein the rear end of the inner conductor is shorted to the trailing end of the outer conductor so that said conductors bounding the insert form a quarter wave stub tuned to a selected frequency.

34. The apparatus defined in claim 26 and further including a dielectric sheath surrounding the outer conductor, said sheath having a leading end spaced rearwardly from the leading end of the outer conductor and a trailing end that extends at least to the trailing end of the outer conductor.

35. Medical catheter apparatus for radiating electromagnetic waves of a first frequency capable of heating tissue and detecting electromagnetic waves of a second frequency emitted by the tissue indicative of tissue temperature, said apparatus comprising a catheter including
an antenna at a distal end of the catheter;
a signal transmitting path to the antenna;
a signal receiving path from the antenna, and
a diplexer connected between said paths inside the catheter, said diplexer including
a quarter wave stub in the form of a shorted transmission line in the signal transmitting path that passes first frequency signals and blocks second frequency signals, and
a filter circuit in the signal receiving path that passes second frequency signals and blocks first frequency signals.

36. Medical catheter apparatus for radiating electromagnetic waves of a first frequency capable of heating tissue and detecting electromagnetic waves of a second frequency emitted by the tissue indicative of tissue temperature, said apparatus comprising a catheter including
an antenna at a distal end of the catheter;
a signal transmitting path to the antenna;
a signal receiving path from the antenna, and
a diplexer connected between said paths inside the catheter, said diplexer including
a quarter wave stub in the form of a shorted transmission line in the signal transmitting path that passes first frequency signals and blocks second frequency signals, said transmission line including a center conductor, and a coaxial conductive insert spaced radially out from the conductor, the conductor and insert each having proximal and distal ends, the distal end of the conductor extending beyond the distal end of the insert to form a part of the antenna and the proximal end of the insert being shorted to the conductor, and
a filter circuit in the signal receiving path that passes second frequency signals and blocks first frequency signals.

37. The apparatus defined in claim 36 and further including a radiometer circuit mounted to the insert and being electrically connected to the filter circuit.

38. The apparatus defined in claim 37 wherein the filter and radiometer circuit comprise one or more monolithic microwave integrated circuit chips.

39. The apparatus defined in claim 36 wherein said antenna includes
an outer conductor having a distal end and surrounding the insert and the distal end of the center conductor, and
a dielectric sheath surrounding the insert but not the distal ends of the center and outer conductors.

40. Medical catheter apparatus for radiating electromagnetic waves of a first frequency capable of heating tissue and detecting electromagnetic waves of a second frequency emitted by the tissue indicative of tissue temperature, said apparatus comprising a catheter including
an electrically conductive insert having proximal and distal ends and an axial passage extending between said ends;
an inner conductor received in said passage, said inner conductor being shorted to the proximal end of the insert and having a distal end extending beyond the distal end of the insert;
an outer conductor surrounding the insert and in electrical contact therewith, said inner and outer conductors forming an antenna at a distal end of the catheter;
a signal transmitting path to the antenna;
a signal receiving path from the antenna, and
a quarter wave stub at said second frequency in the signal transmitting path, said stub including a coaxial transmission line composed of said inner conductor and insert.

41. The apparatus defined in claim 40 and further including a filter circuit that passes second frequency signals and blocks first frequency signals mounted to the insert and being electrically coupled to the inner conductor between the antenna and the stub, said stub and filter circuit together constituting a diplexer inside the catheter.

42. The apparatus defined in the claim 41 and further including a microwave receiver mounted to the insert and being electrically connected to the filter circuit.

43. The apparatus defined in claim 42 wherein the filter circuit and receiver comprise one or more monolithic microwave integrated circuit chips.

* * * * *